United States Patent [19]

Kepley

[11] Patent Number: 5,388,569
[45] Date of Patent: Feb. 14, 1995

[54] PHACOEMULSIFICATION PROBE CIRCUIT WITH SWITCH DRIVE

[76] Inventor: Kevin P. Kepley, 1757 Cargill Dr., Dellwood, Mo. 63136

[21] Appl. No.: 617

[22] Filed: Jan. 5, 1993

Related U.S. Application Data

[63] Continuation-in-part of Ser. No. 940,980, Sep. 4, 1992.

[51] Int. Cl.⁶ ............................................. A61B 8/10
[52] U.S. Cl. ......................................... 601/2; 310/316; 604/22
[58] Field of Search ................. 606/107, 127, 128; 604/22; 128/24 AA; 310/316, 317; 323/351, 285, 287, 282; 330/297; 363/21

[56] References Cited

U.S. PATENT DOCUMENTS

| | | | |
|---|---|---|---|
| 4,378,530 | 3/1983 | Garde | 330/297 |
| 4,587,958 | 5/1986 | Noguchi et al. | 128/24 A |
| 4,793,345 | 12/1988 | Lehmer | 128/303.18 |
| 4,827,911 | 5/1989 | Broadwin | 128/24 AA |
| 4,868,445 | 9/1989 | Wand | 310/316 |
| 5,042,460 | 8/1991 | Sakurai et al. | 128/24 AA |
| 5,121,023 | 6/1992 | Abel | 310/316 |
| 5,151,085 | 9/1992 | Sakurai et al. | 604/22 |
| 5,220,272 | 6/1993 | Nelson | 323/282 |

Primary Examiner—Lee S. Cohen
Assistant Examiner—Brian M. Green

[57] ABSTRACT

A drive for a phacoemulsification probe includes a drive circuit for supplying electrical power to the probe, circuitry for sensing the electrical power supplied by the drive circuit to the probe and for supplying electrical signals indicative of the magnitude of the electrical power supplied. A manually operable input device provides a signal indicative of the transducer power level desired by the user of the probe. A control circuit is responsive to the signal indicative of the desired transducer power level and to the signals indicative of the magnitude of the supplied electrical power for providing control signals to the drive circuit to control the power applied in an efficient manner. The drive circuit includes a totem-pole switch, responsive to at least one of the control signals, to apply power in a square-wave waveform, and a switching regulator for supplying a supply voltage to the totem-pole switch. The totem-pole switch has circuitry associated therewith which is responsive to one of the control signals to initially vary the frequency of the square-wave waveform. The regulator is responsive to a second control signal from the control circuit to vary the voltage supplied by the regulator to the totem-pole switch to control the amplitude of the square-wave waveform. The switching nature of this system substantially minimizes the power consumption of the drive circuit as compared with conventional techniques.

12 Claims, 2 Drawing Sheets

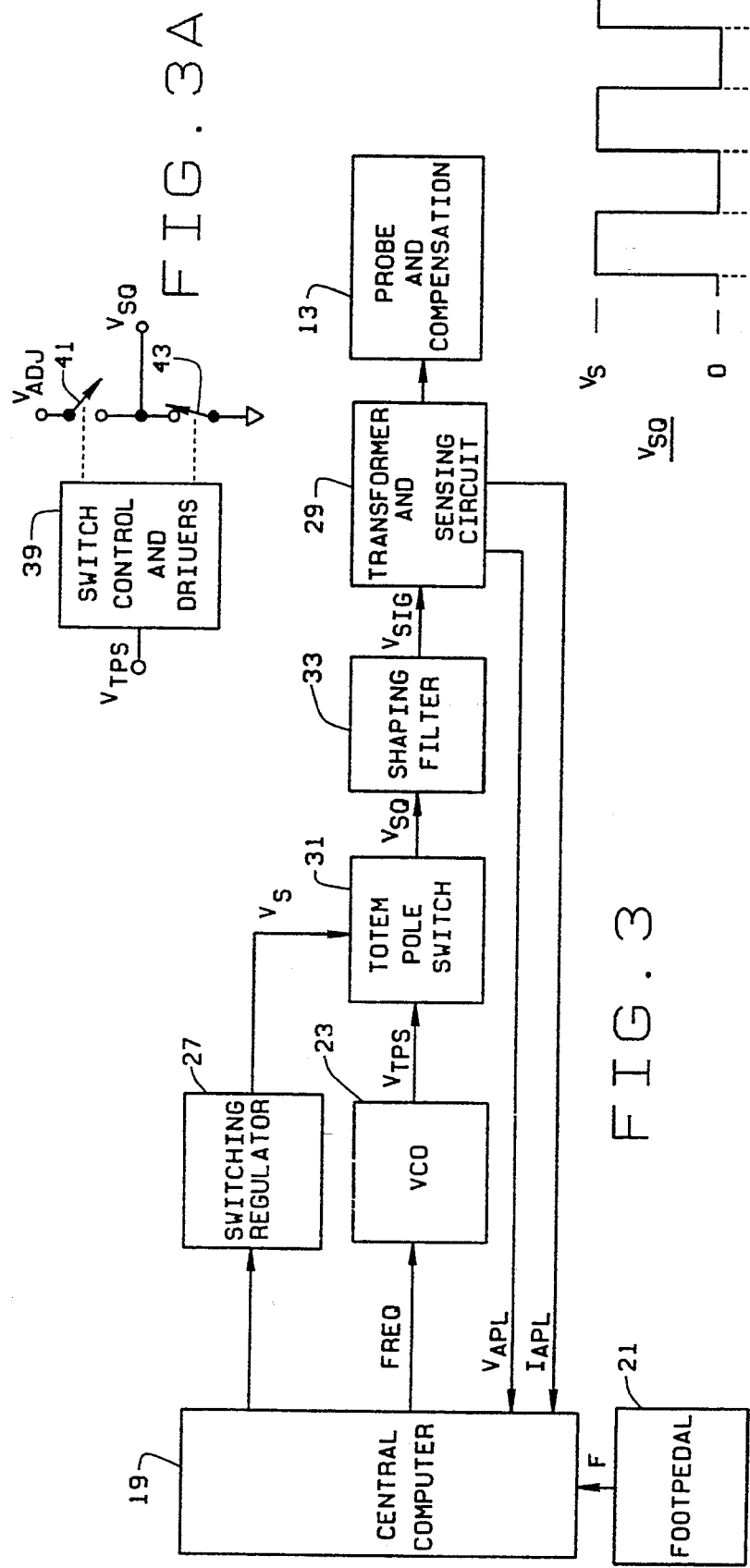
FIG. 3
FIG. 3A
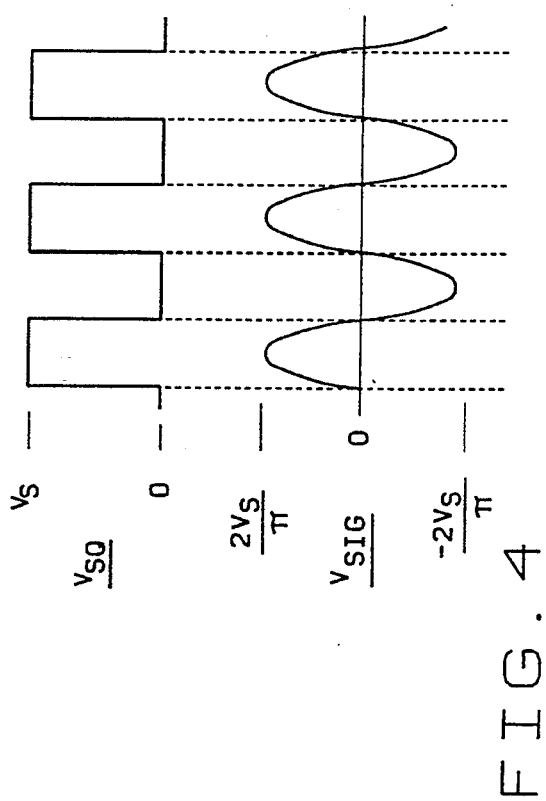
FIG. 4

PHACOEMULSIFICATION PROBE CIRCUIT WITH SWITCH DRIVE

CROSS REFERENCE TO THE RELATED APPLICATION

This is a continuation-in-part application of copending application Ser. No. 07/940,980, filed Sep. 4, 1992.

BACKGROUND OF THE INVENTION

This invention relates to the field of phacoemulsification, and more particularly to drive circuits for phacoemulsification probes.

The use of ultrasonic handpieces or probes for the removal of cataracts in the human eye is well known. Typically, this procedure, called phacoemulsification, uses ultrasonic probes for rupturing cataracts in the eye, combined with aspiration of the resulting debris. Ultrasonic phacoemulsification probes conventionally include a piezoelectric crystal(s) affixed to a probe body. The crystal is driven by an electric power source and converts the electric power to ultrasonic power which is applied by the probe to the cataract.

The amount of power applied by the probe is a function of the frequency and amplitude of the driving electrical waveform and is typically under control of the surgeon using the probe. It is known that the frequency of the applied electrical waveform should be adjusted to the resonant frequency of the probe for efficient power conversion.

Prior art drive circuits for phacoemulsification probes function adequately, but they could be improved. For example, prior art drive circuits have a level of power consumption that is higher than desirable. This high level of power consumption is not only inefficient, it results in other deficiencies. Higher power consumption generates more heat, requiring the use of larger heat sinks than would be desirable, increasing the device's total weight and size, and, possibly, requiring additional cooling fans or other means of dissipating the excess heat.

SUMMARY OF THE INVENTION

Among the various objects and features of the present invention may be noted the provision of a phacoemulsification probe drive circuit with improved efficiency.

A second object is the provision of such a probe drive circuit with reduced power consumption.

A third object is the provision of such a probe drive circuit with reduced size and weight.

Other objects and features will be in part apparent and in part pointed out hereinafter.

Briefly, a phacoemulsification probe system of the present invention includes an ultrasonic handpiece having a distal end of a size suitable for insertion into a patient's eye for emulsifying cataracts and the like. The handpiece includes a transducer for converting electrical power to ultrasonic power for application to the patient. A drive circuit is provided for supplying electrical power to the ultrasonic handpiece transducer. Circuitry is included for sensing the electrical power supplied by the drive circuit to the ultrasonic handpiece transducer and for supplying electrical signals indicative of the magnitude of the electrical power supplied by the drive circuit. A manually operable input device is included for providing a signal indicative of the transducer power level desired by the user of the phacoemulsification probe system. A control circuit is responsive to the signal indicative of the desired transducer power level and to the signals indicative of the magnitude of the supplied electrical power for providing control signals to the drive circuit to control the power applied in an efficient manner. The drive circuit includes a totem-pole switch responsive to at least one of the control signals to apply power in a square-wave waveform, and a switching regulator for supplying a supply voltage to the totem-pole switch. The totem-pole switch has circuitry associated therewith which is responsive to one of the control signals to initially vary the frequency of the square-wave waveform. The regulator is responsive to a second control signal from the control circuit to vary the voltage supplied by the regulator to the totem-pole switch to control the amplitude of the square-wave waveform, thereby controlling the power delivered to the probe. The low source impedance of the totem pole switch substantially reduces the power consumption of the drive circuit, as compared with conventional methods.

A method of the present invention involves driving a phacoemulsification apparatus having an ultrasonic handpiece with a distal end of a size suitable for insertion into a patient's eye for emulsifying cataracts and the like, which handpiece includes a transducer for converting electrical power to ultrasonic power for application to the patient, which apparatus also has a drive circuit connected to the ultrasonic handpiece transducer and a manually operable input device for signaling the desired transducer power level. The drive circuit includes a switching circuit for applying power in a square-wave waveform. The method includes the steps of supplying electrical power from the drive circuit to the ultrasonic handpiece transducer, sensing the electrical power supplied by the drive circuit to the ultrasonic handpiece transducer, comparing the electrical power supplied by the drive circuit with the desired transducer power level, and using a switching regulator to vary the supply voltage to the switching circuit to control the amplitude of the square-wave waveform to efficiently supply the desired power to the transducer. The supply voltage is varied to correspond to the desired output power selected by the manually operable input device.

BRIEF DESCRIPTION OF THE DRAWINGS

FIG. 3 is a block diagram of a second embodiment of the phacoemulsification probe system of the present invention; and FIG. 3A is a schematic of a portion of the circuitry of FIG. 3;

FIG. 4 is a diagram illustrating the square-wave output of a portion of the drive circuit of the system of FIG. 3.

Similar reference characters indicate similar parts throughout the several views of the drawings.

DESCRIPTION OF THE PREFERRED EMBODIMENT

Figure 1:
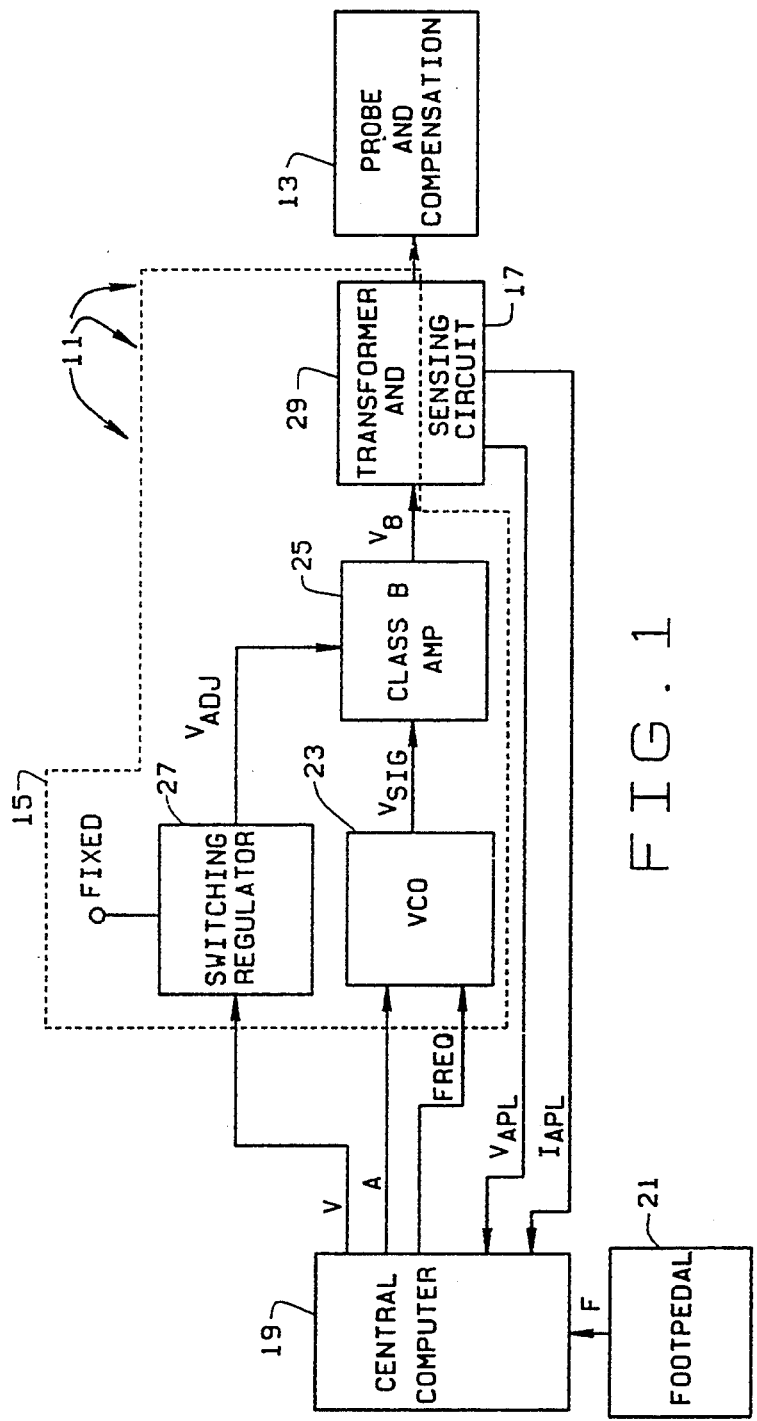
FIG. 1 is a block diagram of the phacoemulsification probe system of the present invention.

Turning to the drawings, a phacoemulsification probe system 11 of the present invention includes an ultrasonic handpiece or probe 13 having a distal end of a size suitable for insertion into a patient's eye for emulsifying cataracts and the like. For purposes of this invention, handpiece 13 may be of any conventional piezoelectric design and includes a conventional transducer for converting electrical power to ultrasonic power for application to the patient (not shown).

A drive circuit 15 is provided for supplying electrical power to the transducer of ultrasonic handpiece 13. The voltage (labelled VAPL on FIG. 1) and current (labelled IAPL) actually supplied by the drive circuit is sensed by conventional voltage and current sensing circuitry 17 and electrical signals representing the applied voltage VAPL and applied current are supplied from the sensing circuitry to a control computer 19. Control computer 19 may be a conventional microprocessor suitably programmed to perform the functions described herein.

In addition to inputs VAPL and IAPL, computer 19 receives an input (labelled F) from a manually operable input device 21. Input device 21 is a conventional footpedal by means of which the surgeon signals the computer to increase or decrease the output power of probe 13.

For purposes of this invention, control computer 19 has three output signals (labelled V, A, and "freq") which are provided to control drive circuit 15. It is known in the art to provide control signals A and "freq" to provide the output power at the desired level and at the resonant frequency of the probe. The present invention is not concerned with control signal "freq" which can be varied as taught in the prior art. Rather it deals with control signals A and V.

Control signals A and "freq" from the control computer are provided to a conventional voltage controlled oscillator 23 whose output is supplied to a class B amplifier 25. Power for the class B amplifier is obtained from a switching regulator 27, and the output of amplifier 25 is supplied to drive a transformer 29. The output of transformer 29 is applied to probe 13 and that same output is sensed by sensing circuit 17 as described above.

Switching regulator 27 provides a supply voltage (labelled VADJ) to amplifier 25 which is a function of the other control signal from computer 19, namely control signal V. In general control signal V is used to control the efficiency of the application of power, specifically to substantially minimize the amplifier's power consumption, while control signal A is used to control the level of power applied to the probe.

Operation of system 11 is as follows: During use of system 11 (after initial adjustment of control signal "freq" to find the resonant frequency of probe 13), control computer 19 receives signal F from footpedal 21, which signal represents the power level the user desires to be applied to probe 13. Computer 19 in response adjusts the amplitude control signal A to voltage controlled oscillator 23 to approximately supply the desired power level to the probe. The actual applied voltage and current VAPL and IAPL are sensed and signals representing them are supplied to computer 19 to close the control loop between the drive circuit and computer 19. The computer uses this information concerning the actual applied power to adjust control signal A as necessary to deliver the desired power corresponding to input signal F to the probe.

Although control of signal A results in the desired power being applied to the probe, it exerts no control over the efficiency of drive circuit 15. To control that efficiency, and thereby substantially minimize the power consumption, computer 19 further adjusts control signal V to switching regulator 27. The switching regulator (preferably a boost regulator, although other types of switching regulators could also be used) is provided with a fixed voltage (labelled VFIXED) which it regulates as commanded by control signal V. Adjustment of control signal V causes the supply voltage output VADJ of the switching regulator to change in a controlled manner.

Figure 2:
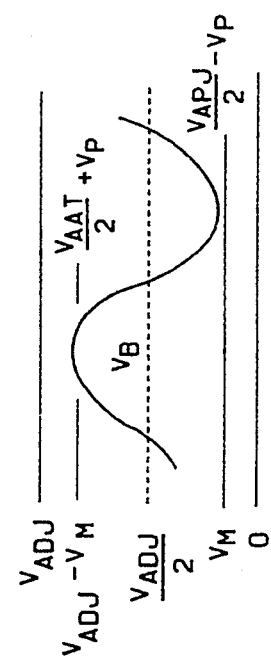
FIG. 2 is a diagram illustrating the voltage levels involved in the system of FIG. 1.

The value of supply voltage VADJ is determined as follows: Referring to FIG. 2, the voltage VB is the signal applied to transformer 29. That signal is a sine wave of amplitude VP. Thus, voltage VB has a peak to peak amplitude of 2*VP. Class B amplifier 25 works in such a way that VB=VADJ/2+VP*sinwt. Computer 19 controls switching regulator 27 so that the supply voltage VADJ remains at the level VADJ=2*VP+2*VM, as VP varies in response to footpedal signal F. VM is the marginal voltage required by the class B amplifier so that the signal is properly passed without significant distortion. If VADJ were larger than this value (2*(VP+VM)), then excess power would be dissipated in amplifier 25. If VADJ were less than this value, then the signal would be distorted.

Turning to FIG. 3, the second embodiment of the present invention is similar to the first, but instead of a class B amplifier 25 it has a totem pole switch 31, followed by a shaping filter 33. In the same manner as the system of FIG. 1, the control computer 19 receives a signal F from the footpedal 21 representing the desired power level to be applied to the probe 13. The control computer then adjusts the amplitude signal A to the switching regulator 27 which controls the magnitude of the supply voltage Vs. The value of Vs in turn determines the amplitude of the square wave Vsq applied to shaping filter 33. The shaping filter (normally a bandpass filter) rejects the harmonics of the square wave (and any DC level) and passes only the fundamental frequency. Output Vsig is thus a sinusoidal signal which is applied to the transformer and sensing circuit 29. Circuit 29 senses the applied voltage and current to the probe, namely Vapl and Iapl. From these signals, the actual power applied to the probe is calculated by the control computer. This allows the control computer to close the control loop and control signal A to deliver the desired power commanded by signal F to the probe.

It should again be understood that the frequency, controlled by signal "freq," is adjusted once at the beginning of the operation to find the resonant frequency of the probe, and then left constant thereafter. Changes in the desired power are made by changing control signal "A."

Turning to FIG. 3A it can be seen that the output from VCO 23 is supplied to the switch control and driver portion 39 of totem-pole switch 31, which in turn open and close switches 41 and 43 to provide the square-wave output shown on the top line of FIG. 4. This square-wave is filtered by shaping filter 33 to provide the sinusoidal waveform Vsig shown on the bottom line of FIG. 4 to the transformer.

It has been found that the systems of the present invention provide greatly increased efficiencies over those of the prior art. For example, with a prior art system, the supply voltage Vs is fixed at some value which is large enough so that the maximum power can be delivered to the load with the largest load resistance. For comparison purposes, assume that all three systems (prior art, FIG. 1, and FIG. 3) are designed to deliver a maximum power of 20 W to a load in the range of 2.2 ohm to 11.1 ohm.

The prior art system must have a supply voltage of 48V in order to be able to deliver maximum power (20W) to the largest resistive load (11.1 ohm). For comparison, the power dissipated in the prior art system is calculated to vary from 8.9W at 11.1 ohm (68.7% efficiency) up to 45.1W at 2.2 ohm (30.7% efficiency). In contrast the system of FIG. 1 has a power dissipation identical to that of the prior art system at 11.1 ohm, but a power dissipation of only 13.6W (59.6% efficiency) at 2.2 ohms. This is almost double the efficiency of the prior art system at low resistance. Even at average load resistance (approximately 4 ohm), the system of FIG. 1 is approximately 20% more efficient than the prior art system.

The system of FIG. 3 is even more efficient. The efficiency varies from about 95% to 99% as the load resistance varies from 2.2 to 11.1 ohms. This is a very significant improvement. The maximum dissipation that must be handled with the system of FIG. 3 is less than a watt. At this level of dissipation, in some applications it may be possible to eliminate a heat sink altogether.

Although the efficiencies mentioned above are theoretical, in practice they can be closely approached, giving the systems of FIGS. 1 and 3 great practical advantages over the prior art. In addition, it should be noted that the efficiencies mentioned above relate to only the amplifier and not to any efficiencies resulting from the use of a switching regulator.

It should be realized that the components described above are illustrative only. Any number of similar components could be used with the same invention. Numerous variations of the present constructions and methods may be used. The examples given herein are merely illustrative, and are not to be construed in a limiting sense.

What is claimed is:

1. A phacoemulsification probe system comprising:
   an ultrasonic handpiece having a distal end of a size suitable for insertion into a patient's eye for emulsifying cataracts, said handpiece including a transducer for converting electrical power to ultrasonic power for application to the patient;
   drive circuit means for supplying electrical power to the ultrasonic handpiece transducer;
   means for sensing the electrical power supplied by the drive circuit means to the ultrasonic handpiece transducer and for supplying electrical signals indicative of the magnitude of said electrical power supplied by the drive circuit means;
   manually operable input means for providing a signal indicative of a transducer power level desired by the user of the phacoemulsification probe system; and
   control circuit means responsive to the signal indicative of the desired transducer power level and to the signals indicative of the magnitude of the supplied electrical power for providing control signals to the drive circuit means to control the power applied in an efficient manner;
   said drive circuit means including switching means responsive to at least one of the control signals to apply power in a square-wave waveform, and regulator means for supplying a supply voltage to the switching means, said switching means including means responsive to said one of the control signals to initially vary the frequency of the square-wave waveform, said regulator means being responsive to a second control signal from the control circuit means to vary the magnitude of the supply voltage supplied by the regulator means to the switching means to control the amplitude of the square-wave waveform, the frequency of the square-wave waveform being held fixed by the switching means while the magnitude of the supply voltage is varied, thereby controlling the power delivered to the probe.

2. The phacoemulsification probe system as set forth in claim 1 wherein the switching means includes an oscillator directly responsive to said one of the control signals for initially setting the frequency of the square-wave waveform, said control signal controlling the frequency of oscillation of the oscillator.

3. The phacoemulsification probe system as set forth in claim 2 wherein the square-wave waveform has approximately a fifty percent duty cycle.

4. The phacoemulsification probe system as set forth in claim 1 wherein for a fixed frequency of the square-wave waveform, the control circuit means controls the regulator means to supply the supply voltage at a magnitude selected to provide the desired transducer power level to the transducer.

5. The phacoemulsification probe system as set forth in claim 1 wherein the regulator means is a switching regulator whose output voltage is controlled by the second control signal from the control circuit means.

6. The phacoemulsification probe system as set forth in claim 1 wherein the output of the switching means is connected to a shaping filter, the output of the shaping filter being connected to the input of a transformer, the output of the transformer being connected to drive the ultrasonic handpiece transducer, said means for sensing the electrical power supplied to the ultrasonic handpiece being connected to the transformer to sense said supplied electrical power.

7. The phacoemulsification probe system as set forth in claim 1 wherein the switching means includes a totem-pole switch.

8. The phacoemulsification probe system as set forth in claim 7 wherein the totem pole switch has substantially lower source impedance than conventional class A, class B, and class AB amplifiers, thereby significantly improving the power efficiency of the drive circuit means.

9. A method of driving a phacoemulsification apparatus having an ultrasonic handpiece with a distal end of a size suitable for insertion into a patient's eye for emulsifying cataracts, said handpiece including a transducer for converting electrical power to ultrasonic power for application to the patient, said apparatus also having a drive circuit connected to the ultrasonic handpiece transducer and also having a manually operable input device for signaling a desired transducer power level, said drive circuit including switching means for applying power in a square-wave waveform, said method comprising:
   supplying electrical power from the drive circuit to the ultrasonic handpiece transducer;
   sensing the electrical power supplied by the drive circuit to the ultrasonic handpiece transducer;
   comparing the electrical power supplied by the drive circuit with the desired transducer power level; and
   supplying a supply voltage to the switching means and using a switching regulator to vary the magnitude of the supply voltage supplied to the switching means to control the amplitude of the square-wave waveform to efficiently supply power to the transducer, the magnitude of said supply voltage being varied to correspond to the desired output power selected by the manually operable input device, the square-wave waveform having a frequency which is held unchanged while the magnitude of the supply voltage is varied.

10. The method as set forth in claim 9 wherein the power supplying step includes supplying a square-wave waveform from the switching means which has approximately a fifty percent duty cycle.

11. The method as set forth in claim 9 wherein the frequency of the square-wave waveform is fixed for a given use and the switching regulator is controlled to supply the supply voltage at a magnitude selected to provide the desired transducer power level to the transducer.

12. The method as set forth in claim 9 wherein the square-wave waveform is filtered to change the waveform substantially into a sine wave waveform before application thereof to the transducer.

* * * * *

UNITED STATES PATENT AND TRADEMARK OFFICE
CERTIFICATE OF CORRECTION

PATENT NO. : 5,388,569
DATED : Feb. 14, 1995
INVENTOR(S) : Kevin P. Kepley

It is certified that error appears in the above-indentified patent and that said Letters Patent is hereby corrected as shown below:

The Assignee was not listed. Please list the Assignee as follows:

Assignee: American Cyanamid Company
Stamford, CT

Claim 11, column 8, line 5, delete "switching" and insert -- means -- after the word regulator.

Signed and Sealed this

Twentieth Day of June, 1995

Attest:

BRUCE LEHMAN

Attesting Officer

Commissioner of Patents and Trademarks